(12) United States Patent
Brown

(10) Patent No.: US 7,769,605 B2
(45) Date of Patent: *Aug. 3, 2010

(54) MULTIPLE PATIENT MONITORING SYSTEM FOR PROACTIVE HEALTH MANAGEMENT

(75) Inventor: Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/843,727

(22) Filed: Aug. 23, 2007

(65) Prior Publication Data

US 2007/0299326 A1    Dec. 27, 2007

Related U.S. Application Data

(63) Continuation of application No. 11/484,211, filed on Jul. 11, 2006, which is a continuation of application No. 10/233,296, filed on Aug. 30, 2002, which is a continuation-in-part of application No. 09/880,735, filed on Jun. 12, 2001, now abandoned, which is a continuation of application No. 09/152,353, filed on Sep. 14, 1998, now Pat. No. 6,246,992, which is a continuation-in-part of application No. 08/732,158, filed on Oct. 16, 1996, now Pat. No. 5,832,448.

(51) Int. Cl.
*A61B 5/00* (2006.01)
*G06F 19/00* (2006.01)

(52) U.S. Cl. ......................................................... 705/3

(58) Field of Classification Search ........................ None
See application file for complete search history.

(56) References Cited

U.S. PATENT DOCUMENTS 3,426,150 A    2/1969    Tygart (Continued)

FOREIGN PATENT DOCUMENTS

EP    0286456    10/1988

(Continued)

OTHER PUBLICATIONS

Albiser, A.M. "Intelligent Instrumentation in Diabetic Management". CRC Critical Reviews in Biomedical Engineering. vol. 17, No. 1, pp. 1-24.*

(Continued)

*Primary Examiner*—Gerald J. O'Connor
*Assistant Examiner*—Sheetal R Rangrej
(74) *Attorney, Agent, or Firm*—Suiter Swantz pc llo

(57) ABSTRACT

A system and method for monitoring a group of patients having a chronic disease or ongoing health condition. The method includes the step of collecting from each patient a corresponding set of measurements of a control parameter of the health condition. Each set of measurements has a collection date. A control value is calculated for each patient from the corresponding set of measurements. The method further includes the steps of generating and displaying a group overview chart having one data point for each patient. Each data point indicates the control value calculated for the corresponding patient and a time period which has elapsed since the collection date of the patient's corresponding set of measurements. In a preferred embodiment, the method includes the additional steps of selecting from the group overview chart at least one of the patients represented thereon and transmitting supervisory instructions to the at least one selected patient.

9 Claims, 6 Drawing Sheets

U.S. PATENT DOCUMENTS

| | | |
|---|---|---|
| 3,566,365 A | 2/1971 | Rawson et al. |
| 3,566,370 A | 2/1971 | Worthington, Jr. et al. |
| 3,581,072 A | 5/1971 | Nymeyer |
| 3,768,014 A | 10/1973 | Smith |
| 3,811,116 A | 5/1974 | Takeuchi et al. |
| 3,883,235 A | 5/1975 | Lynn et al. |
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,051,522 A | 9/1977 | Healy et al. |
| 4,060,915 A | 12/1977 | Conway |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,412,287 A | 10/1983 | Braddock, III |
| 4,417,306 A | 11/1983 | Citron et al. |
| 4,422,081 A | 12/1983 | Woods |
| 4,428,733 A | 1/1984 | Kumar-Misir |
| 4,449,536 A | 5/1984 | Weaver |
| 4,465,077 A | 8/1984 | Schneider |
| 4,473,884 A | 9/1984 | Behl |
| 4,518,361 A | 5/1985 | Conway |
| 4,519,398 A | 5/1985 | Lisiecki et al. |
| 4,531,527 A | 7/1985 | Reinhold, Jr. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,627,445 A | 12/1986 | Garcia |
| 4,674,652 A | 6/1987 | Aten et al. |
| 4,686,624 A | 8/1987 | Blum et al. |
| 4,694,490 A | 9/1987 | Harvey et al. |
| 4,695,954 A | 9/1987 | Rose et al. |
| 4,712,562 A | 12/1987 | Ohayon et al. |
| 4,722,349 A | 2/1988 | Baumberg |
| 4,729,381 A | 3/1988 | Harada et al. |
| 4,730,253 A | 3/1988 | Gordon |
| 4,731,726 A | 3/1988 | Allen, III |
| 4,738,451 A | 4/1988 | Logg |
| 4,768,229 A | 8/1988 | Benjamin et al. |
| 4,779,199 A | 10/1988 | Yoneda et al. |
| 4,782,511 A | 11/1988 | Nemec et al. |
| 4,789,928 A | 12/1988 | Fujisaki |
| 4,796,639 A | 1/1989 | Snow et al. |
| 4,799,156 A | 1/1989 | Shavit et al. |
| 4,799,199 A | 1/1989 | Scales, III et al. |
| 4,803,625 A * | 2/1989 | Fu et al. ..................... 600/483 |
| 4,835,372 A | 5/1989 | Gombrich et al. |
| 4,838,275 A | 6/1989 | Lee |
| 4,846,797 A | 7/1989 | Howson et al. |
| 4,853,521 A | 8/1989 | Claeys et al. |
| 4,858,354 A | 8/1989 | Gettler |
| 4,858,617 A | 8/1989 | Sanders |
| 4,890,621 A | 1/1990 | Hakky |
| 4,894,777 A | 1/1990 | Negishi et al. |
| 4,897,869 A | 1/1990 | Takahashi |
| 4,899,839 A | 2/1990 | Dessertine et al. |
| 4,903,201 A | 2/1990 | Wagner |
| 4,907,973 A | 3/1990 | Hon |
| 4,916,441 A | 4/1990 | Gombrich |
| 4,931,934 A | 6/1990 | Snyder |
| 4,933,873 A | 6/1990 | Kaufman et al. |
| 4,933,876 A | 6/1990 | Markoff et al. |
| 4,950,246 A | 8/1990 | Muller |
| 4,950,264 A | 8/1990 | Osborn, III |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,978,303 A | 12/1990 | Lampbell |
| 4,978,335 A | 12/1990 | Arthur, III |
| 4,979,509 A | 12/1990 | Hakky |
| 5,007,429 A | 4/1991 | Treatch et al. |
| 5,009,645 A | 4/1991 | Silver et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,035,625 A | 7/1991 | Munson et al. |
| 5,036,462 A | 7/1991 | Kaufman et al. |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia |
| 5,068,536 A | 11/1991 | Rosenthal |
| 5,074,317 A | 12/1991 | Bondell et al. |
| 5,077,476 A | 12/1991 | Rosenthal |
| 5,077,665 A | 12/1991 | Silverman et al. |
| 5,095,798 A | 3/1992 | Okada et al. |
| 5,104,380 A | 4/1992 | Holman et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,552 A | 7/1992 | Fang et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,143,378 A | 9/1992 | Joel |
| 5,171,977 A | 12/1992 | Morrison |
| 5,176,502 A | 1/1993 | Sanderson et al. |
| 5,182,707 A | 1/1993 | Cooper et al. |
| 5,204,670 A | 4/1993 | Stinton |
| 5,219,322 A | 6/1993 | Weathers |
| 5,222,020 A | 6/1993 | Takeda |
| 5,226,895 A | 7/1993 | Harris |
| 5,227,874 A | 7/1993 | Von Kohorn |
| 5,228,450 A | 7/1993 | Sellers |
| 5,230,629 A | 7/1993 | Buschke |
| 5,231,990 A | 8/1993 | Gauglitz |
| 5,243,515 A | 9/1993 | Lee |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,282,950 A | 2/1994 | Dietze et al. |
| 5,295,491 A | 3/1994 | Gevins |
| 5,299,121 A | 3/1994 | Brill et al. |
| 5,301,105 A | 4/1994 | Cummings, Jr. |
| 5,304,112 A | 4/1994 | Mrklas et al. |
| 5,304,468 A | 4/1994 | Phillips et al. |
| 5,307,263 A | 4/1994 | Brown |

| Patent | Date | Name |
|---|---|---|
| 5,309,919 A | 5/1994 | Snell et al. |
| 5,321,009 A | 6/1994 | Baeder et al. |
| 5,325,288 A | 6/1994 | Satou |
| 5,329,459 A | 7/1994 | Kaufman et al. |
| 5,329,608 A | 7/1994 | Bocchieri et al. |
| 5,331,549 A | 7/1994 | Crawford, Jr. |
| 5,333,981 A | 8/1994 | Pronovost et al. |
| 5,335,338 A | 8/1994 | Proesel |
| 5,339,821 A | 8/1994 | Fujimoto |
| 5,341,291 A | 8/1994 | Roizen et al. |
| 5,343,239 A | 8/1994 | Lappington et al. |
| 5,344,324 A | 9/1994 | O'Donnell et al. |
| 5,357,427 A | 10/1994 | Langen et al. |
| 5,366,896 A | 11/1994 | Margrey et al. |
| 5,368,562 A | 11/1994 | Blomquist et al. |
| 5,371,687 A | 12/1994 | Holmes, II et al. |
| 5,375,604 A | 12/1994 | Kelly et al. |
| 5,377,100 A | 12/1994 | Pope et al. |
| 5,390,238 A | 2/1995 | Kirk et al. |
| 5,399,821 A | 3/1995 | Inagaki et al. |
| 5,410,471 A | 4/1995 | Alyfuku et al. |
| 5,410,474 A | 4/1995 | Fox |
| 5,429,140 A | 7/1995 | Burdea et al. |
| 5,431,690 A | 7/1995 | Schaldach et al. |
| 5,431,691 A | 7/1995 | Snell et al. |
| 5,434,611 A | 7/1995 | Tamura |
| 5,438,607 A | 8/1995 | Przygoda, Jr. et al. |
| 5,438,983 A | 8/1995 | Falcon |
| 5,441,047 A | 8/1995 | David et al. |
| 5,449,334 A | 9/1995 | Kingsbury |
| 5,454,721 A | 10/1995 | Kuch |
| 5,454,722 A | 10/1995 | Holland et al. |
| 5,456,606 A | 10/1995 | McIntyre |
| 5,456,692 A | 10/1995 | Smith, Jr. et al. |
| 5,458,123 A | 10/1995 | Unger |
| 5,467,269 A | 11/1995 | Flaten |
| 5,471,039 A | 11/1995 | Irwin, Jr. et al. |
| 5,471,382 A | 11/1995 | Tallman et al. |
| 5,483,276 A | 1/1996 | Brooks et al. |
| 5,488,412 A | 1/1996 | Majeti et al. |
| 5,488,423 A | 1/1996 | Walkingshaw et al. |
| 5,501,231 A | 3/1996 | Kaish |
| 5,502,636 A | 3/1996 | Clarke |
| 5,502,726 A | 3/1996 | Fischer |
| 5,504,519 A | 4/1996 | Remillard |
| 5,517,405 A | 5/1996 | McAndrew et al. |
| 5,518,001 A | 5/1996 | Snell |
| 5,519,058 A | 5/1996 | Gonick et al. |
| 5,519,433 A | 5/1996 | Lappington et al. |
| 5,523,232 A | 6/1996 | Sechler |
| 5,536,249 A | 7/1996 | Castellano et al. |
| 5,542,420 A | 8/1996 | Goldman et al. |
| 5,544,649 A | 8/1996 | David et al. |
| 5,546,943 A | 8/1996 | Gould |
| 5,549,117 A | 8/1996 | Tacklind et al. |
| 5,550,575 A | 8/1996 | West et al. |
| 5,553,609 A * | 9/1996 | Chen et al. .................. 600/301 |
| 5,558,638 A | 9/1996 | Evers et al. |
| 5,564,429 A | 10/1996 | Bornn et al. |
| 5,569,212 A | 10/1996 | Brown |
| 5,572,421 A | 11/1996 | Altman et al. |
| 5,572,646 A | 11/1996 | Kawai et al. |
| 5,574,828 A | 11/1996 | Hayward et al. |
| 5,576,952 A | 11/1996 | Stutman et al. |
| 5,583,758 A | 12/1996 | McIlroy et al. |
| 5,590,648 A | 1/1997 | Mitchell et al. |
| 5,593,349 A | 1/1997 | Miguel et al. |
| 5,593,390 A | 1/1997 | Castellano et al. |
| 5,594,637 A | 1/1997 | Eisenberg et al. |
| 5,596,994 A | 1/1997 | Bro |
| 5,597,307 A | 1/1997 | Redford et al. |
| 5,601,435 A | 2/1997 | Quy |
| 5,613,495 A | 3/1997 | Mills et al. |
| 5,619,991 A | 4/1997 | Sloane |
| 5,624,265 A | 4/1997 | Redford et al. |
| 5,628,309 A | 5/1997 | Brown |
| 5,629,981 A | 5/1997 | Nerlikar |
| 5,631,844 A | 5/1997 | Margrey et al. |
| 5,633,910 A | 5/1997 | Cohen |
| 5,635,532 A | 6/1997 | Samid |
| 5,640,569 A | 6/1997 | Miller et al. |
| 5,640,953 A | 6/1997 | Bishop et al. |
| 5,642,731 A | 7/1997 | Kehr |
| 5,642,936 A | 7/1997 | Evans |
| 5,651,363 A | 7/1997 | Kaufman et al. |
| 5,651,775 A | 7/1997 | Walker et al. |
| 5,659,691 A | 8/1997 | Durward et al. |
| 5,666,487 A | 9/1997 | Goodman et al. |
| 5,670,711 A | 9/1997 | Detournay et al. |
| 5,675,635 A | 10/1997 | Vos et al. |
| 5,678,562 A | 10/1997 | Sellers |
| 5,678,571 A | 10/1997 | Brown |
| 5,679,075 A | 10/1997 | Forrest et al. |
| 5,680,590 A | 10/1997 | Parti |
| 5,680,866 A | 10/1997 | Kangas et al. |
| 5,687,322 A | 11/1997 | Deaton et al. |
| 5,687,717 A | 11/1997 | Halpern et al. |
| 5,687,734 A | 11/1997 | Dempsey et al. |
| 5,689,652 A | 11/1997 | Lupien et al. |
| 5,692,906 A | 12/1997 | Corder |
| 5,704,364 A | 1/1998 | Saltzstein et al. |
| 5,704,366 A | 1/1998 | Tacklind et al. |
| 5,704,902 A | 1/1998 | Vandenbelt et al. |
| 5,704,922 A | 1/1998 | Brown |
| 5,710,178 A | 1/1998 | Samid |
| 5,710,918 A | 1/1998 | Lagarde et al. |
| 5,711,297 A | 1/1998 | Iliff |
| 5,714,319 A | 2/1998 | Joutel et al. |
| 5,715,451 A | 2/1998 | Marlin |
| 5,715,823 A | 2/1998 | Wood et al. |
| 5,717,739 A | 2/1998 | Dyer et al. |
| 5,717,913 A | 2/1998 | Driscoll |
| 5,720,733 A | 2/1998 | Brown |
| 5,722,418 A | 3/1998 | Bro |
| 5,727,153 A | 3/1998 | Powell |
| 5,730,124 A | 3/1998 | Yamauchi |
| 5,730,654 A | 3/1998 | Brown |
| 5,732,696 A | 3/1998 | Rapoport et al. |
| 5,732,709 A | 3/1998 | Tacklind et al. |
| 5,734,413 A | 3/1998 | Lappington et al. |
| 5,749,083 A | 5/1998 | Koda et al. |
| 5,752,234 A | 5/1998 | Withers |
| 5,754,740 A | 5/1998 | Fukuoka et al. |
| 5,760,771 A | 6/1998 | Blonder et al. |
| 5,772,585 A | 6/1998 | Lavin et al. |
| 5,778,882 A | 7/1998 | Raymond et al. |
| 5,782,814 A | 7/1998 | Brown et al. |
| 5,785,650 A | 7/1998 | Akasaka et al. |
| 5,787,295 A | 7/1998 | Nakao |
| 5,791,342 A | 8/1998 | Woodard |
| 5,792,117 A | 8/1998 | Brown |
| 5,793,969 A | 8/1998 | Kamentsky et al. |
| 5,794,219 A | 8/1998 | Brown |
| 5,794,251 A | 8/1998 | Watanabe et al. |
| 5,796,393 A | 8/1998 | MacNaughton et al. |
| 5,799,318 A | 8/1998 | Cardinal et al. |
| 5,800,458 A | 9/1998 | Wingrove |
| 5,802,494 A | 9/1998 | Kuno |
| 5,802,534 A | 9/1998 | Hatayama et al. |
| 5,806,057 A | 9/1998 | Gormley et al. |
| 5,810,747 A | 9/1998 | Brudny et al. |
| 5,819,735 A | 10/1998 | Mansfield et al. |
| 5,822,544 A | 10/1998 | Chaco et al. |
| 5,822,715 A | 10/1998 | Worthington et al. |
| 5,825,283 A | 10/1998 | Camhi |
| 5,827,180 A | 10/1998 | Goodman |

| | | |
|---|---|---|
| 5,828,943 A | 10/1998 | Brown |
| 5,832,448 A | 11/1998 | Brown |
| 5,835,896 A | 11/1998 | Fisher et al. |
| 5,840,020 A | 11/1998 | Heinonen et al. |
| 5,842,976 A | 12/1998 | Williamson |
| 5,868,669 A | 2/1999 | Iliff |
| 5,868,683 A | 2/1999 | Protopapas et al. |
| 5,875,432 A | 2/1999 | Sehr |
| 5,879,163 A | 3/1999 | Brown et al. |
| 5,882,338 A | 3/1999 | Gray |
| 5,887,133 A | 3/1999 | Brown et al. |
| 5,893,077 A | 4/1999 | Griffin |
| 5,893,098 A | 4/1999 | Peters et al. |
| 5,897,493 A | 4/1999 | Brown |
| 5,899,855 A | 5/1999 | Brown |
| 5,911,687 A | 6/1999 | Sato et al. |
| 5,913,310 A | 6/1999 | Brown |
| 5,918,603 A | 7/1999 | Brown |
| 5,920,477 A | 7/1999 | Hofbert et al. |
| 5,933,136 A | 8/1999 | Brown |
| 5,935,060 A | 8/1999 | Iliff |
| 5,940,801 A | 8/1999 | Brown |
| 5,941,829 A | 8/1999 | Saltzstein et al. |
| 5,945,651 A | 8/1999 | Chorosinski et al. |
| 5,951,300 A | 9/1999 | Brown |
| 5,954,641 A | 9/1999 | Kehr et al. |
| 5,956,501 A | 9/1999 | Brown |
| 5,960,403 A | 9/1999 | Brown |
| 5,961,446 A | 10/1999 | Beller et al. |
| 5,966,526 A | 10/1999 | Yokoi |
| 5,971,855 A | 10/1999 | Ng |
| 5,971,922 A | 10/1999 | Arita et al. |
| 5,983,003 A | 11/1999 | Lection et al. |
| 5,983,217 A | 11/1999 | Khosravi-Sichani et al. |
| 5,987,471 A | 11/1999 | Bodine et al. |
| 5,995,969 A | 11/1999 | Lee et al. |
| 5,997,476 A | 12/1999 | Brown |
| 5,997,502 A | 12/1999 | Reilly et al. |
| 6,001,065 A | 12/1999 | DeVito |
| 6,022,315 A | 2/2000 | Iliff |
| 6,022,615 A | 2/2000 | Rettenbacher |
| 6,023,686 A | 2/2000 | Brown |
| 6,024,281 A | 2/2000 | Shepley |
| 6,029,138 A | 2/2000 | Khorasani et al. |
| 6,032,119 A | 2/2000 | Brown et al. |
| 6,035,328 A | 3/2000 | Soukal |
| 6,046,761 A | 4/2000 | Echerer |
| 6,049,794 A | 4/2000 | Jacobs et al. |
| 6,050,940 A | 4/2000 | Braun et al. |
| 6,055,314 A | 4/2000 | Spies et al. |
| 6,055,487 A | 4/2000 | Margery et al. |
| 6,055,506 A | 4/2000 | Frasca, Jr. |
| 6,057,758 A | 5/2000 | Dempsey et al. |
| 6,068,615 A | 5/2000 | Brown et al. |
| 6,095,985 A | 8/2000 | Raymond et al. |
| 6,101,478 A | 8/2000 | Brown |
| 6,110,148 A | 8/2000 | Brown et al. |
| 6,113,578 A | 9/2000 | Brown |
| 6,138,145 A | 10/2000 | Kawanaka |
| 6,144,837 A | 11/2000 | Quy |
| 6,151,586 A | 11/2000 | Brown |
| 6,161,095 A | 12/2000 | Brown |
| 6,167,362 A | 12/2000 | Brown et al. |
| 6,167,386 A | 12/2000 | Brown |
| 6,168,563 B1 | 1/2001 | Brown |
| 6,177,940 B1 | 1/2001 | Bond et al. |
| 6,186,145 B1 | 2/2001 | Brown |
| 6,189,029 B1 | 2/2001 | Fuerst |
| D439,242 S | 3/2001 | Brown et al. |
| 6,210,272 B1 | 4/2001 | Brown |
| 6,221,012 B1 | 4/2001 | Maschke et al. |
| 6,233,539 B1 | 5/2001 | Brown |
| 6,240,393 B1 | 5/2001 | Brown |
| 6,248,065 B1 | 6/2001 | Brown |
| 6,260,022 B1 | 7/2001 | Brown |
| 6,270,455 B1 | 8/2001 | Brown |
| 6,270,456 B1 | 8/2001 | Iliff |
| 6,334,778 B1 | 1/2002 | Brown |
| 6,352,523 B1 | 3/2002 | Brown et al. |
| 6,368,273 B1 | 4/2002 | Brown |
| 6,370,513 B1 | 4/2002 | Kolawa et al. |
| 6,375,469 B1 | 4/2002 | Brown |
| 6,379,301 B1 | 4/2002 | Worthington et al. |
| 6,381,577 B1 | 4/2002 | Brown |
| 6,436,036 B1 | 8/2002 | Miller-Kovach et al. |
| 6,513,532 B2 | 2/2003 | Mault et al. |
| 2002/0019748 A1 | 2/2002 | Brown |
| 2004/0106855 A1 | 6/2004 | Brown |
| 2004/0107116 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |

FOREIGN PATENT DOCUMENTS

| | | |
|---|---|---|
| EP | 0320749 | 6/1989 |
| EP | 370599 | 5/1990 |
| EP | 0461910 | 12/1991 |
| EP | 508912 | 10/1992 |
| EP | 526166 | 2/1993 |
| EP | 0558975 | 9/1993 |
| EP | 0653718 | 5/1995 |
| EP | 676709 | 10/1995 |
| EP | 680727 | 11/1995 |
| EP | 761160 | 3/1997 |
| EP | 08131551 | 12/1997 |
| EP | 0251520 | 1/1998 |
| GB | 2218831 | 11/1989 |
| GB | 2225637 | 6/1990 |
| JP | 54005785 | 1/1979 |
| JP | 54146633 | 11/1979 |
| JP | 62226278 | 10/1987 |
| JP | 5155024 | 6/1993 |
| JP | 5266002 | 10/1993 |
| JP | 1995407095963 | 4/1995 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9302622 | 2/1993 |
| WO | WO-9416774 | 8/1994 |
| WO | WO-95/09386 | 4/1995 |
| WO | WO-95/20199 | 7/1995 |
| WO | WO-9522131 | 8/1995 |
| WO | WO-9529447 | 11/1995 |
| WO | WO-96/07908 | 3/1996 |
| WO | WO-96/25877 | 8/1996 |
| WO | WO-9636923 | 11/1996 |
| WO | WO-97/08605 | 3/1997 |
| WO | WO-97/12544 | 4/1997 |
| WO | WO-9737738 | 10/1997 |
| WO | WO-98/16895 | 4/1998 |
| WO | WO-9831275 | 7/1998 |
| WO | WO-9839933 | 9/1998 |

OTHER PUBLICATIONS

+5V Powered Isolated RS-232 Drivers/Receivers Maxim Integrated Products.
Adilman; "Videogames: Knowing the Score"; Creative Computing; v9; p. 224(5); Dec. 1983; Dialog: File 148, Acc#01891055.
AdOptimizer—Ad Management Software For Websites, Newsbytes, pNEW10040041, Oct. 4, 1996.
Albisser, A.M. "Intelligent Instrumentation in Diabetic Management", CRC Critical Reviews in Biomedical Engineering, vol. 17, No. 1, pp. 1-24.

Anonymous, "Health Hero Network, Inc. Receives First-Ever FDA Clearance for Connecting Medical Devices to Internet", PR Newswire, (Dec. 2, 1993), 3 pages.

Antique Collector, Putting the Lot on the Net, vol. 66, Issue 9, p. 26, Downloaded from Corporate Resource Net, Nov./Dec. 1995.

Bai, "Design of home healthcare network", IEEE 1997 pp. 1657-1658.

Billiard, A., et al. "Telematic Transmission of Computerized Blood Glucose Profiles for IDDm Patients", Diabetes Care, (Feb. 1991), vol. 14, No. 2, pp. 130-134.

Blood Glucose Monitors, Portable Health Device, (1998), vol. 17(9), pp. 253-271.

Bower, "Brain Clues to Energy-efficient Learning", Science News, (Apr. 1992), v. 141; p. 215(1); Dialog: File 647, Acct# 12123949.

Brenman et al.; "Interaction of Nitric Oxide Synthase with the Postsynaptic Density Protein PSD-95 and α1-Syntrophin Mediated by PDZ Domains"; Cell; vol. 84, pp. 757-767, Mar. 8, 1996; Ref: XP-002104701.

Bruce, "Health Hero Network CEO, CNNfn", Digital Jam, (Dec. 1, 1999), 3.

Bruce, et al., "The Effects of Sympathetic Nervous System Activation and Psychological Stress . . . "; Diabetologia; 35(9); 1992; 835-843; Dialog: File 5, Acc#9629427. (9 pages).

Brunetti, P., et al., "A Simulation Study on a Self-Turning Portable Controller of Blood Glucose", The International Journal of Artificial Organs, (1993), vol. 16, No. 16, pp. 51-57.

Caprihan, A., et al., "A Simple Microcomputer for Biomedical Signal Processing", IECI '78 Annual Conference Proceedings on Industrial Applications of Microprocessors, (Mar. 20, 1978), 18-23.

Cathay Pacific Airways-USA receives more than 1,300 bids during first five days of CyberAuction; Business Wire, Oct. 18, 1995, p. 10181119.

Cathay Pacific Airways-USA to Hold First-Ever Internet CyberAuction; CyberTravelers Can Bid for 50 Business Class Round Trips to Hong Kong—No Minimum Bid; Business Wire; p. 9261084; Sep. 26, 1995; Dialog: File 148, Acc#08167091.

CD-ROM Mavericks: Proprietary TV-Based Players, Byte Guide to CD-ROM, pp. 100-105.

Central Fetal Monitoring Systems with Optical Disk Storage, New Technology Brief, (Nov./Dec. 1998), vol. 2, No. 6, pp. 249-251.

Cheng, Joe H., "PCT Search Report", (Jan. 11, 1996).

DigiPet Instruction Manual, 1997.

Digital Doggie; retrieved from URL http://www.virtualpet.com/vp/farm/gigapet/ddoggie.htm Apr. 23, 2000.

Douglas, A.S., et al., "Hand-Held Glucose Monitor and Recorder", Proceedings of the Annual International Conference of the IEEE Engineering in Medicine and Biology Society, New Orleans, LA, (Nov. 1988), pp. 747-748.

Edelson; "Fashion Reevaluates Flickering Fortunes of TV Home Shopping"; WWD; v170 n87; p. 1(3); Nov. 8, 1995; Dialog: File 148, Acc#08289119.

EP European Search Report, From 6858P005EP, (Mar. 27, 1998).

Fabietti, P.G., et al., "Wearable System for Acquisition, Processing and Storage of the Signal from Amperometric Glucose Sensors", The International Journal of Artificial Organs, (1991), vol. 14, No. 3, pp. 175-178.

Finston, "Parent + Teacher = Healthy Child", Diabetes Forecast, (Apr. 1994), v47 n9; p. 26(5); Dialog: file 149, Acc# 15804228.

Fox, "Not My Type: Type B Behavior, Type I Diabetes Plus Stress Equals Blood Sugar Blues", Health, (Mar. 1998), v20 n3; pp. 22(1); Dialog: File 149, Acc# 06397959.

Franklin; "Proposed Auction Rules for PCS: The FCC Plans to Use Competitive Bidding, but Exact Procedures are Undefined"; Cellular Business; v10 n13; p. 18(2); Dec. 1993; Dialog: File 148, Acc#06787310.

Frieberger, Paul, "Video Game Takes on Diabetes Superhero 'Captain Novolin' Offers Treatment Tips", San Francisco Examiner, (Jun. 26, 1992), Fourth Edition, Business Section B1.

Furnham, et al; "Measuring Locus of Control: a Critique of General Children's Health- and Work-related Locus of Control Questionnaires"; British Journal of Psychology; v84 n4; p. 443(37); Nov. 1993; Dialog: File 88, Acc# 14903135.

Future of the Virtual Pet Industry, 1997 [retrieved on Apr. 23, 2000], Retrieved from <URL:www.virtualpet.com/vp/ future/future.htm>.

Gardner, et al.; "Comprehension and Appreciation of Humorous Material Following Brain Damage"; Brain; Sep. 1975; 98(3); pp. 399-412; Dialog: File 153, Acc#02859983. (14 pages).

Gauntlet (for PC) rulebook by Mindscape Inc. (Gauntlet by Apple);1985.

Giga Farm; retrieved from URL http://www.virtualpet.com/vp/farm/gigapet/gpfarm/gpfarm.htm Apr. 23, 2000.

Giga Pets, 1997 [retrieved on Apr. 23, 2000], Retrieved from <URL:www.virtualpet.com/vp/farm/gigapet/gigapet.htm>.

Gordon; "Auctions Become High Tech"; Dealer Business; v29 n7; p. 21(4); Mar. 1995; Dialog: File 148, Acc#07862519.

Guiffrida, et al., Should We Pay the Patient? Review of Financial Incentives to enhance Patient Compliance:, Biomedical Journal, (1997), vol. 315, pp. 703-707.

Hauben, Jay R., "A Brief History of the Cleveland Free-Net", available at http://www.ais.org/~irh/acn7-1.a09.html, (1995) pp. 1-4.

Hauser, et al., "Will Computers Replace or Complement the Diabetes Educator?", The Medical Journal of Australia, (Oct. 5, 1992), vol. 157, 489-491.

Horio, Hiroyuki, et al., "Clinical Telecommunication Network System for Home Monitoring", Medical & Biological Engineering & Computing, (Mar. 1994), vol. 32, 227-230.

How Flash Memory Works, Internet printout of URL address: http://www.howstuffworks.com/flash-memory4.htm, (Sep. 28, 2002), 2 pages.

Howey, et al., "A Rapidly Absorbed Analogue of Human Insulin"; Diabetes, vol. 43, Mar. 1994, pp. 396-402. (7 pages).

Hunter, "Technological Advances in Bedside Monitoring: Biosensors", Archives and Laboratory Medicine, (Jul. 1987), pp. 633-636.

Hutheesing, Nikhil, "An on-line gamble", Forbes, v157 n10 p. 288(1), May 20, 1996.

Introducing the Next Generation of About Your Diabetes, U.S. Pharmacopical Convention and American Diabetes Association, (1993).

Jaffrey et al.; "PIN: An Associated Protein Inhibitor of Neuronal Nitric Oxide Synthase"; Science; vol. 274; Nov. 1, 1996; Ref: XP 002050141.

Jimison et al., "Patient-Specific explanation in models of chronic disease", Revised Feb. 1992 Artificial Intelligence in Medicine 4 (1992) 191-205.

Jones, Chris, "Microsoft readies DocObject; technology will allow document editing in Web browsers", InfoWorld, v18 n18 p. 48(1), Apr. 29, 1996.

Kauffmann, et al., "Epidemiological Study of the Genetics and Environment of Asthma, Bronchial Hyperresponsiveness and Atrophy", Am. J. Respir. Crit. Care Med., (1997), vol. 156, pp. S123-S129.

Kaufman, Steven, B., "The Learning Game", Nation's Business, (Nov. 1993).

Kennedy et al.; "Television Computer Games: A New Look in Performance Testing"; Aviat Space Environ Med; Jan. 1982, 53(1); pp. 49-53. (5 pages); Dialog Abstract: File 155, Acc#0353751.

Kuykendall, V.G., et al., "Assessment of Self-Monitored Blood Glucose results Using a Reflectance Meter with Memory and Microcomputer", Symposium on Computer Applications in Medical Care, (Jan. 1981), vol. 70, pp. 98-102.

Lachnit, Carroll, "Hawkin's Online Auction", Photo District News, vol. 16, Issue 1, p. 18, Jan. 1996.

Lacyk, John, "PCT Search Report", (Jun. 12, 1997).

Latman, N.S., "Evaluation of Electronic, Digital Blood Glucose Monitors", Biomedical Instrumentation and Technology, (1991), vol. 25, No. 1, 43-49.

Leyerle, Beverly J., et al., "The PDMS as a Focal Point for Distributed Patient Data", International Journal of Clinical Monitoring and Computing, (1988), vol. 5, pp. 155-161.

Luebke, Cathy, "Barrett-Jackson Auction Turns High-Tech", Business Journal, vol. 16, Issue 12, pp. 11, Jan. 19, 1996.

Makikawa, M., et al., "Microprocessor-Based Memory Device for Ambulatory Heart Rate and Physical Activity Recording", Methods of Information in Medicine, (1994), vol. 33, No. 1, pp. 94-96.

Marsh, David G. "Approaches Toward the Genetic Analysis of Complex Traits Asthma and Atrophy", Am. J. Respir.Crit.Care Med., (1997), vol. 156, pp. S-133-S138.

Martinez, Fernando D., "Complexities of the Genetics of Asthma", Am.J. Respir. Crit. Care Med., (1997), vol. 156, pp. S117-S122.

Marx, Wendy, "More than just the Scores: ESPNET SportsZone is a model for expanding brand names online", InformationWeek, n576 p. 61(2), Apr. 22, 1996.

Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 01624462.

McCullagh, PJ et al., "Computerized paradigms for eliciting the contingent negative variation event-related potential," Proceedings of the Annual International Conference of the Engineering in Medicine & Biology Society, IEEE, Conf. 14, p. 2481-2483, Oct. 1992.

Meissner, et al., "Building an Integrated Clinical and Research Network", Proceedings of the SPIE, (Oct. 24, 1995), vol. 2618, p. 92-99.

Miles, Laughton E., "A Portable Microcomputer for Long-Term Physiological Monitoring in the Home and Work Environment", Medical Monitoring in the Home and Work Environment, (1990), pp. 47-57.

Mims; "Psychological Testing"; Computers & Electronics; v23; p. 22(6); Feb. 1985; Dialog: File 47, Acc# 2654858.

Moore, "New Applications Break Through Storage Boundaries", Computer Technology Review, (Oct. 1999), vol. 19, No. 10 p. 1.

Mule. rulebook by Electronic Arts, 1983.

Nano Baby Instructions; retrieved from file://C:\My Documents\Nano Baby Instructions.htm Apr. 23, 2000.

Nano Fighter Pets; retrieved from URL http://www.virtualpet.com/vp/farm/nano/nfighter.htm Apilr 23, 2000.

Nano Page, 1997 [retrieved on Apr. 23, 2000], Retrieved from <URL:www.virtualpet.com/vp/farm/nano/nano.htm>.

Octhigotchi Instruction Manual, 1997. Dino-Kun Instruction Manual, 1997.

O'Donnell; "Alan's At It Again"; Bond Buyer; v309 n29448; p. 1(3); Jul. 21, 1994; Dialog: File 148, Acc#07478152.

Onsale Joins Fray as Online Shopping Picks Up Speed: Internet Booms; Computer Reseller News; Jun. 5, 1995; p. 73; Dialog: File 16, Acc#05649796.

Onsale Onsale Brings Thrill of Auctions and Bargain Hunting Online; Unique Internet retail service debuts with week-long charity auction for the Computer Museum in Boston, May 24, 1995; Dialog Abstract: File 610, Acc#0489267.

Pfeiffer, E. F., "The Glucose Sensor: The Missing Link in Diabetes Therapy", Hormone and Metabolic Research, (1990), vol. 24m Suppl. pp. 154-164.

Playmates Toys deals knockout blow to virtual pet competitors with introduction of Nano Fighter™ For Boys; New Nano Pet Fighting Pet Press Release; retrieved from URL http://www.virtualpet.com/vp/farm/nano/nfightpr.htm Apr. 23, 2000.

Playmates Toys leads Americas virtual pet craze into its next generation by introducting talking Nano Pals; Talking Nano Pet Press Release; Nov. 18, 1997; retrieved from URL http://www.virtualpet.com/vp/farm/nano/talkn/tnpress.htm on Apr. 23, 2000.

Poitout, V., et al. "A Glucose Monitoring System for On Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.

Polson, Gary "Recent Developments and Trends in Keychain Virtual Pets," 1997 [retrieved on Apr. 23, 2000], Retrieved from <URL:www.virtualpet.com/vp/future/trendsla.htm>.

Potter, David, "Fundamentals of PC-Based Data Acquisition", Sensors, (Feb. 1994), pp. 12-20.

Reis, H, "Telemedicine: Transmitting Expertise to the Point of Care Toward an Electronic Patient Record"; '97, Nashville, TN, Apr. 27-May 3, 1997, pp. 248-256, v. 3.

Research project launched to improve health of America's communities; new Disney community in Florida is focus of program. Business Wire, p. 10011142. Oct. 1, 1996.

Results of the world's first on-line auction, http://www.christies.com.

RO_AUCTION Auctioneers Property Database System and RO_AUCTION Auctioneers Accounting System; RO-Auction features; Dec. 4, 1995.

Roberts; "Diabetes and Stress: A Type A Connection?", Psychology Today, (Jul. 1987), v. 21; pp. 22(1); Dialog: File 149, Acc# 05038381.

Rose, V. L., et al., "Decentralized Testing for Prothrombin Time and Activated Partial Thromboplastin Time Using a Dry Chemistry Portable Analyser", Archives of Pathology and Laboratory Medicine, (Jun. 1993), vol. 117, pp. 611-617.

Save the earth artrock auction, http://www.commerce.com.saveearth. Auction Web, http://www.ebay.com.

Schement, "An Intelligent Controller for Neurophysiological Experiments," Proceeding of the Annual Symposium on Computer Based Medical Systems, Durham, Jun. 14-17, 1992, p. 528, line 1-p. 529, line 21.

Schenkels, P., "Supplementary European Search Report", Application No. EP 97 92 2716, (Mar. 11, 2002).

Schork, Nicholas J., "Genetics of Complex Disease", Am.J.Respir. Crit. Care Me., (1997), vol. 156, pp. S103-S109.

Schrezenmeir, J. et al., "Computer Assisted Insulin Dosage Adjustment—Perspective for Diabetes Control", Hormone and Metabolic Research, Supplement Series, (1990), vol. 24, pp. 116-123.

Seigmann;"Nowhere to Go but Up"; PC Week; v12 n42, p. A5(1); Oct. 23, 1995; Dialog: File 148, Acc#08222496.

Seybold—New Horizons teams with Duke, Real Media; The Seybold Report on Desktop Publishing, v10 n12 p. 24(1), Aug. 12, 1996.

Shandle, Jack, "Who Will Dominate the Desktop in the 90's?", , Electronics, Feb. 1990, pp. 48-50. (3 pages) Cited by 2 patents.

Shults, Marc C., et al., "A Telemetry-Instrumentation System for Monitoring Multiple Subcutaneously Implanted Glucose Sensors", IEEE Transactions on Biomedical Engineering, (Oct. 1994), vol. 41, No. 10, pp. 937-942.

Skolnick et al. "Simultaneous Analysis of Multiple Polymorphic Loci Using Amplified Sequence Polymorphisms (ASPs)"; Genomics. 2: 273-279.

Soeldner, J. S., "Treatment of Diabetes Mellitus by Devices", The American Journal of Medicine, (Jan. 1981), vol. 70, 183-194.

Spitzer et al.; "The moderating effect of age on self-care"; Western Journal of Nursing Research, v18, n2, p. 136(13), Apr. 1996.

Symbol Technologies; "Healthcare Mobility Solutions for the PPT8800", Feb. 2004.

Talking Nano Puppy; retrieved from URL http://www.virtualpet.com/vp/farm/nano/talkn/talkn.htm Apr. 23, 2000.

Tamagotchi, 1997 [retrieved on Apr. 23, 2000], Retrieved from <URL:www.virtualpet.com/vp/farm/lleg/lleg.htm>.

Tandy Radio Shack , "The description of the Tandy Radio Shack TRS-80 Model 100/102 device available at http://www.oldcomputuers.com/musuem/computer.asp?c=233", World Wide Web, (Feb. 13, 2004), 1-3.

Telemedicine Provides Two-Way Computer Link for Parents of Very Premature Infants. PR Newswire. p. 1007NEM034. Oct. 7, 1996.

Theme Hospital, product review 1996 [retrieved Apr. 21, 2000], Retrieved from <URL:www.vigilante.co.uk/ep/misc/hospital.htm>.

Towards a partnership of care, M2 Presswire, Jun. 14, 2000.

United Healthcare's OPTUM Division goes online to better health by announcing a unique internet application. PR Newswire, p. 0801MNTH004. Aug. 1, 1996.

Updike, Stuart J., et al., "Laboratory Evaluation of New Reusable Blood Glucose Sensor", Diabetes Care, (Nov./Dec. 1998), vol. 11, No. 10, pp. 801-807.

Valla, et al., "A Structured Pictorial Questionnaire to Assess DSM-III-R-based Diagnosis in Children (6-11 years)"; Journal of Abnormal Child Psychology; v22 n4; p. 403(21); Aug. 1994; Dialog: File 88, Acc# 15759542.

Vallera, D. A., et al., "Accuracy of Portable Blood Glucose Monitoring", American Journal of Clinical Pathology, (1991), vol. 95, No. 2, pp. 247-252.

Virtual Pet Product Reviews, 1997 [retrieved on Apr. 23, 2000], Retrieved from <URL:www.virtualpet.com/vp/farm/reviews/reviews,htm>.

Virtual Tomagutchi, 1998 [retrieved Apr. 23, 2000], Retrieved from <URL:www.sttf.org/english/action/tomagutchi.html>.

Voelker, Rebecca, "Shoe Leather Therapy is Gaining on TB", Jama, (Mar. 13, 1996), vol. 275, 743.

Wilkins, Aaron. "Expanding Internet access for health care consumers", Health Care Management Review, Summer, Jul. 1999, 24-30.

Wyatt, J. C., "Clinical Data Systems, Part 2: Components and Techniques", Lancet, (Dec. 1994), vol. 344, No. 8937, pp. 1609-1614.

Yoshizawa, Daisuke, et al., "The Development of a Data Processing System with Personal Computer SX Standard System for Flow Injection Analysis", Journal of Flow Injection Analysis, (1988), V.5, No. 2, pp. 101-110.

Matthews et al, "Analysis of Serial Measurements in Medical Research", BMJ, Jan. 27, 1990; vol. 300, pp. 230-235.

Alere Medical Inc 's First Supplemental Response to Plaintiffs Amended Interrogatory No. 2. Jun. 20, 2008.

U.S. Appl. No. 90/010,053—Order Granting Request for Ex Parte Reexamination, Jan. 18, 2008.

* cited by examiner

78

| TO: | << INSERT PATIENT MAIL ADDRESS >> |
| SUBJECT: | REQUEST FOR BLOOD GLUCOSE MEASUREMENTS |

Hello << INSERT PATIENT NAME >>,

I have not received your blood glucose measurements since << INSERT COLLECTION DATE >> and I am concerned that your blood glucose level stay in control. Please transmit your latest measurements to the clinic today.

Sincerely,

Dr. Peters

| TO: | << INSERT PATIENT MAIL ADDRESS >> |
| SUBJECT: | MEASURE YOUR BLOOD GLUCOSE REGULARLY |

Hello << INSERT PATIENT NAME >>,

Your last set of blood glucose measurements did not include an adequate number of measurements to assess your progress in controlling diabetes. Please remember to test your blood glucose regularly so that we may work together to keep your diabetes in control.

Sincerely,

Dr. Peters

This is Dr. Peters calling from the Medical Clinic for << INSERT PATIENT NAME >>. If this is <<INSERT PATIENT NAME>>, press 1.

I have not received your blood glucose measurements since << INSERT COLLECTION DATE >> and I am concerned that your blood glucose level stay in control. Please transmit your latest measurements to the clinic today.

MULTIPLE PATIENT MONITORING SYSTEM FOR PROACTIVE HEALTH MANAGEMENT

CROSS REFERENCE TO RELATED APPLICATIONS

The present application is a continuation of U.S. patent application Ser. No. 11/484,211 filed Jul. 11, 2006 which is a continuation of U.S. patent application Ser. No. 10/233,296 filed Aug. 30, 2002 which is a continuation-in-part of U.S. patent application Ser. No. 09/880,735 filed Jun. 12, 2001, (abandoned) which is a continuation of U.S. patent application Ser. No. 09/152,353 filed Sep. 14, 1998, now U.S. Pat. No. 6,246,992 which is a continuation-in-part of U.S. patent application Ser. No. 08/732,158 filed Oct. 16, 1996, now U.S. Pat. No. 5,832,448. Said U.S. patent application Ser. Nos. 11/484,211, 10/233,296, 09/880,735, 09/152,353 and 08/732,158 are hereby incorporated by reference in their entirety.

FIELD OF THE INVENTION

The present invention relates generally to computer systems for managing healthcare, and in particular to a system and method for proactively monitoring a group of patients having a chronic disease or ongoing health condition.

BACKGROUND OF THE INVENTION

Managing a chronic disease or ongoing health condition requires the monitoring and controlling of a physical or mental parameter of the health condition. Examples of these parameters include blood glucose in diabetes, respiratory flow in asthma, blood pressure in hypertension, cholesterol in cardiovascular disease, weight in eating disorders, T-cell or viral count in HIV, and frequency or timing of episodes in mental health disorders. Because of the continuous nature of these health conditions, their corresponding parameters must be monitored and controlled on a regular basis by the patients themselves outside of a medical clinic.

Typically, the patients monitor and control these parameters in clinician assisted self-care or outpatient treatment programs. While these outpatient treatment programs offer significant advantages for patients and healthcare providers, they present the assisting clinician with two problems in effectively managing the medical priorities of his or her patients.

The first problem is in determining each patient's current medical status. Since the patients themselves monitor their health conditions, the clinician is often limited to learning each patient's status strictly through patient initiated events, such as an emergency visit or the delivery of the patient's latest medical data. Even with the current availability of remote monitoring devices that store and transmit medical data from a patient's home to a clinic, the clinician must still wait for medical information whose arrival depends on the patient's initiative.

As a result, the majority of the clinician's time is spent with the patients who are the most motivated and eager for a response, while the greatest medical needs remain with the unmotivated patients who do not visit the clinician or transmit their medical data. These unmotivated patients often develop urgent medical needs that could have been prevented with proper medical management. Consequently, the cost of treating their chronic health conditions is much higher than one might expect given the sophistication of current medical monitoring devices.

The second problem is in determining which patients are having the greatest difficulty in controlling their health condition so that the clinician may focus attention on these patients. Unfortunately, most existing healthcare information systems are only designed to display medical data on an individual patient basis. Few systems have been developed that enable clinician's to view medical data for an entire group of patients simultaneously. Consequently, it is extremely difficult for a clinician to prioritize his or her time and efforts in a manner that optimizes care and minimizes costs and complications for the entire group of patients.

Many systems have been developed for remote monitoring of a group of patients. For example, U.S. Pat. No. 5,357,427 issued to Langen et al. on Oct. 18, 1994 describes a system for simultaneous remote monitoring of a group of high risk patients using artificial intelligence. The system includes for each patient a remote monitoring device, such as a blood pressure cuff, glucometer, etc. The remote monitoring device is connected to a telemedical interface box which transmits monitored data over a telephone line to a data recording system. Data is also collected from each patient using an artificial intelligence program that asks the patient questions through a telephone. A computer is connected to the recording system to display individual patient messages indicating a current symptom of one of the patients.

Although Langen's system does allow simultaneous monitoring of a group of patient's, it lacks a display mechanism for simultaneously displaying summary data for the entire group of patients. Langen's system also lacks a mechanism for indicating which patients have been out of contact with the clinician and therefore have an unknown current medical status. Consequently, Langen's system is ineffective in aiding the clinician to prioritize his or her time and efforts in managing the medical priorities of an entire group of patients.

Another medical monitoring system designed to monitor a group of patients is disclosed in U.S. Pat. No. 5,331,549 issued to Crawford on Jul. 19, 1994. Crawford's system includes a plurality of vital signs monitors for monitoring a plurality of patients, each monitor providing continuous data to a central server. A supervisory screen is connected to the server to display a normal status or varying levels of alarm status of the vital signs of individual patients. The system permits an overview display of a hospital floor as well as a zoom in display of an individual patient site. The system further provides a warning alarm signal when any one or more vital signs of an individual patient is outside of a predetermined limit.

While Crawford's system does allow simultaneous viewing of the vital sign status of each patient in a group, it is only directed at monitoring a group of patients who are continually connected to their vital sign monitors. Crawford's overview screen lacks any mechanism for indicating which patients have been out of contact with a clinician since continual contact is assumed.

Further, the summary data presented for each patient on the overview screen is limited to an indication of a normal state or alarm state of each patient's vital signs. Consequently, the system only allows a clinician to determine which patients are having the greatest difficulty in controlling their health condition when an actual emergency situation exists. Thus, Crawford's system is effective as a medical alarm system, but of little use to a clinician in managing the medical priorities of a group of patients who are not continually monitored in a healthcare facility.

OBJECTS AND ADVANTAGES OF THE INVENTION

In view of the above, it is an object of the present invention to provide a multiple patient monitoring system that allows a clinician to view and manage the medical priorities of an entire group of patients having a chronic health condition. It is another object of the invention to provide a multiple patient monitoring system that allows a clinician to communicate proactively with unmotivated patients who have lost contact with the clinician. A further object of the invention is to provide a multiple patient monitoring system that allows a clinician to optimize efforts and minimize costs in managing the medical needs of the entire group of patients.

These and other objects and advantages will become more apparent after consideration of the ensuing description and the accompanying drawings.

SUMMARY OF THE INVENTION

The invention presents a system and method for monitoring a group of patients having a chronic disease or ongoing health condition. The method includes the step of collecting from each patient a corresponding set of measurements of a control parameter of the health condition. Each set of measurements has a corresponding collection date. For each patient, a control value is calculated from the corresponding set of measurements, the control value indicating the patient's control over the health condition. In the preferred embodiment, the control value calculated for each patient comprises a mean value of the patient's corresponding set of measurements.

The method also includes the step of determining for each patient a time period which has elapsed since the collection date of the patient's corresponding set of measurements. The method further includes the steps of generating and displaying a group overview chart having a plurality of data points. Each of the data points on the chart represents one corresponding patient and indicates the control value and the time period determined for the corresponding patient.

In the preferred embodiment, the method includes the additional steps of selecting from the group overview chart at least one of the patients represented thereon and transmitting supervisory instructions to the at least one selected patient. In one embodiment, the supervisory instructions are transmitted in an electronic mail message. In another embodiment, the supervisory instructions are transmitted in an automated telephone message.

A preferred system for implementing the method of the invention includes a plurality of recording devices, such as remote monitoring devices or electronic logbooks, for recording the corresponding set of measurements for each patient. The system also includes a master patient database for receiving and storing each set with a corresponding collection date. A communication network connects the recording devices to the master patient database and transmits the recorded sets of measurements therebetween.

A processor is connected to the database for determining for each of the patients the control value and time period elapsed since the collection date of the patient's corresponding set of measurements. The processor further includes a chart generation application for generating the group overview chart. A display is connected to the processor for displaying the group overview chart.

In the preferred embodiment, a selection device, such as a mouse or keyboard, is connected to the processor for selecting from the group overview chart at least one of the patients represented thereon. In this embodiment, the processor further includes an automated response application for transmitting supervisory instructions to the at least one selected patient. In one embodiment, the automated response application comprises a mail merge application for generating and transmitting the supervisory instructions in an electronic mail message. In another embodiment, the automated response application comprises an automated telephone call processing application for transmitting the supervisory instructions in a telephone message.

BRIEF DESCRIPTION OF THE DRAWINGS

FIGS. 4-5 are sample electronic mail messages containing supervisory instructions for a patient.

DESCRIPTION

Figure 1:
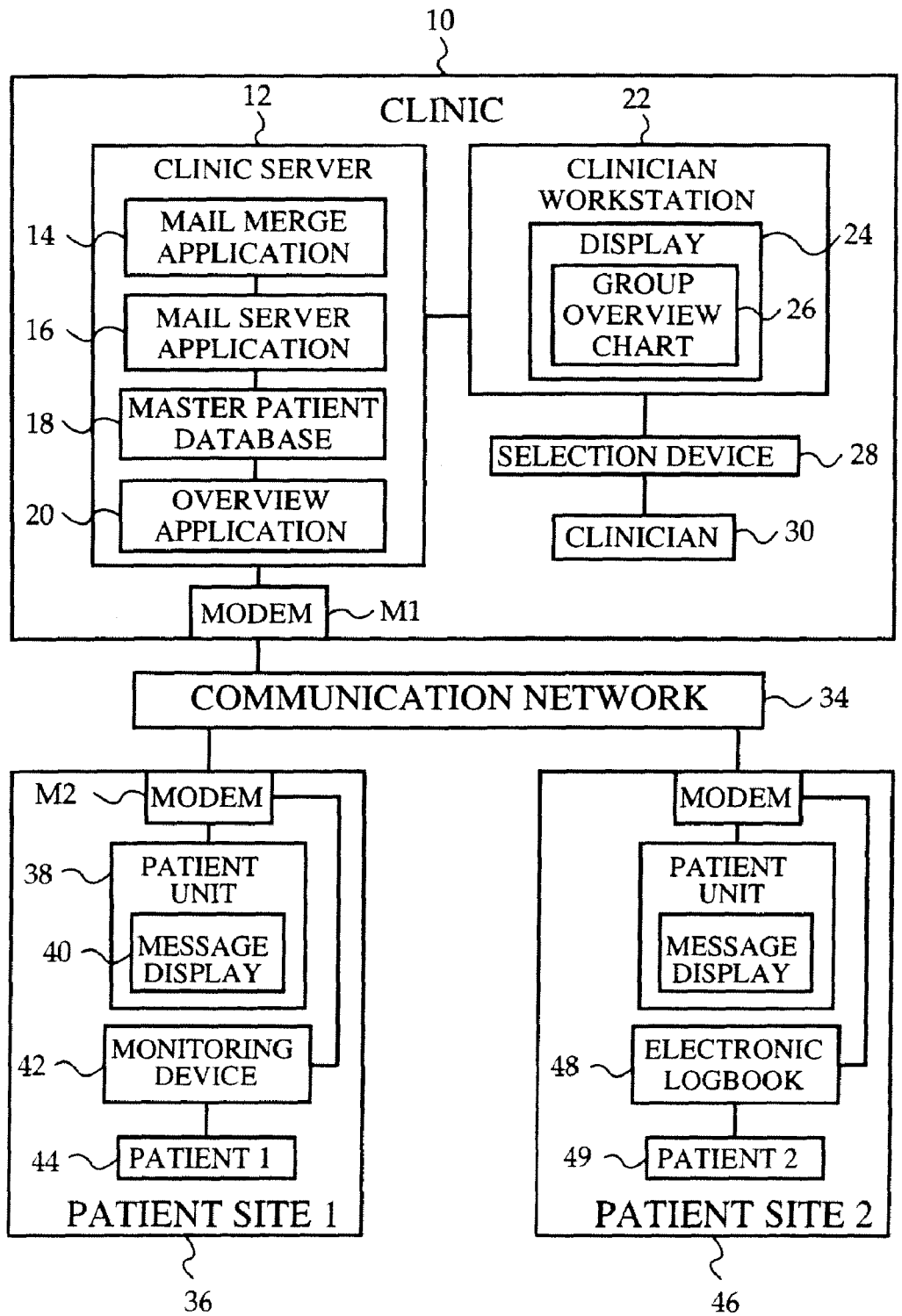
FIG. 1 is a schematic block diagram of a multiple patient monitoring system according to the invention.

A preferred embodiment of the invention is illustrated in FIGS. 1-6. FIG. 1 shows the main components of a system for monitoring a group of patients having an ongoing health condition. A healthcare clinic 10 has a clinic server computer 12 that includes a mail merge application 14, a mail server application 16, a master patient database 18, and a patient overview application 20. Mail merge application 14 is designed to generate electronic mail messages containing supervisory instructions to selected patients in the group, as will be explained in the operation section below. Mail server application 16 is a conventional electronic mail server designed to transmit the generated electronic mail messages to the selected patients.

Master patient database 18 is for storing patient data relating to each patient managed by clinic 10. Overview application 20 is a controlling software application for performing various calculations using the patient data stored in master patient database 18 and for generating a group overview chart with the patient data, as will be explained in detail below. Clinic server 12 is coupled to a modem M1 for connecting server 12 to a communication network 34, preferably a public telephone network or similar data transmission network.

A clinician workstation 22 is networked to clinic server 12. Clinician workstation 22 is preferably a personal computer or network terminal. Workstation 22 has a display 24 for displaying to a clinician 30 a group overview chart 26. Workstation 22 further includes a user selection device 28, such as a mouse or keyboard, for selecting patients represented on group overview chart 26 to receive supervisory instructions from clinician 30.

A patient unit 38 for receiving electronic mail messages from mail server 16 is located at a first patient site 36, typically the patient's home. Patient unit 38 includes a message display 40 for displaying the electronic mail messages. In the preferred embodiment, patient unit 38 is a personal computer having a display monitor. However, in alternative embodiments, patient unit 38 may be any information processing and display unit, such as a network terminal, a television set with a set-top cable converter box, a personal digital assistant, or a video game system. Patient unit 38 is connected to a modem M2 such that patient unit 38 is networked to communication network 34.

A recording device, such as a remote monitoring device 42, is also connected to modem M2. Device 42 is for collecting from a first patient 44 a corresponding set of measurements of a control parameter of the patient's health condition, such as blood glucose levels for a diabetic patient, peak flow rates for an asthmatic patient, or blood pressure for a hypertension patient. Device 42 is capable of recording each measurement in the set with a corresponding measurement date and measurement time. Device 42 is designed to record the set of measurements and transmit the recorded set to database 18 through communication network 34. Such monitoring devices for recording and transmitting measurements of a parameter of a health condition are well known in the art.

A second patient site 46 includes the same equipment as first patient site 36, with the exception of the recording device used by a second patient 49. The recording device at second patient site 46 is an electronic logbook 48 for recording a corresponding set of measurements entered in logbook 48 by second patient 49. Logbook 48 is capable of recording each measurement in the set with a corresponding measurement date and measurement time. Logbook 48 is designed to transmit the set of measurements recorded therein to database 18 through communication network 34. Such electronic logbooks for recording and transmitting data are well known in the art. The use of logbook 48 to record and transmit patient data enables those patients with mental health conditions or other condition whose control parameters may not be physically measured to participate in the patient monitoring system.

For simplicity of illustration, only two patient sites and two corresponding patients are shown in FIG. 1. It is obvious that the system of the invention may be effectively used to monitor a great number of patients. In a typical implementation, hundreds of patient sites are connected to clinic server 12 via communication network 34.

Figure 2:
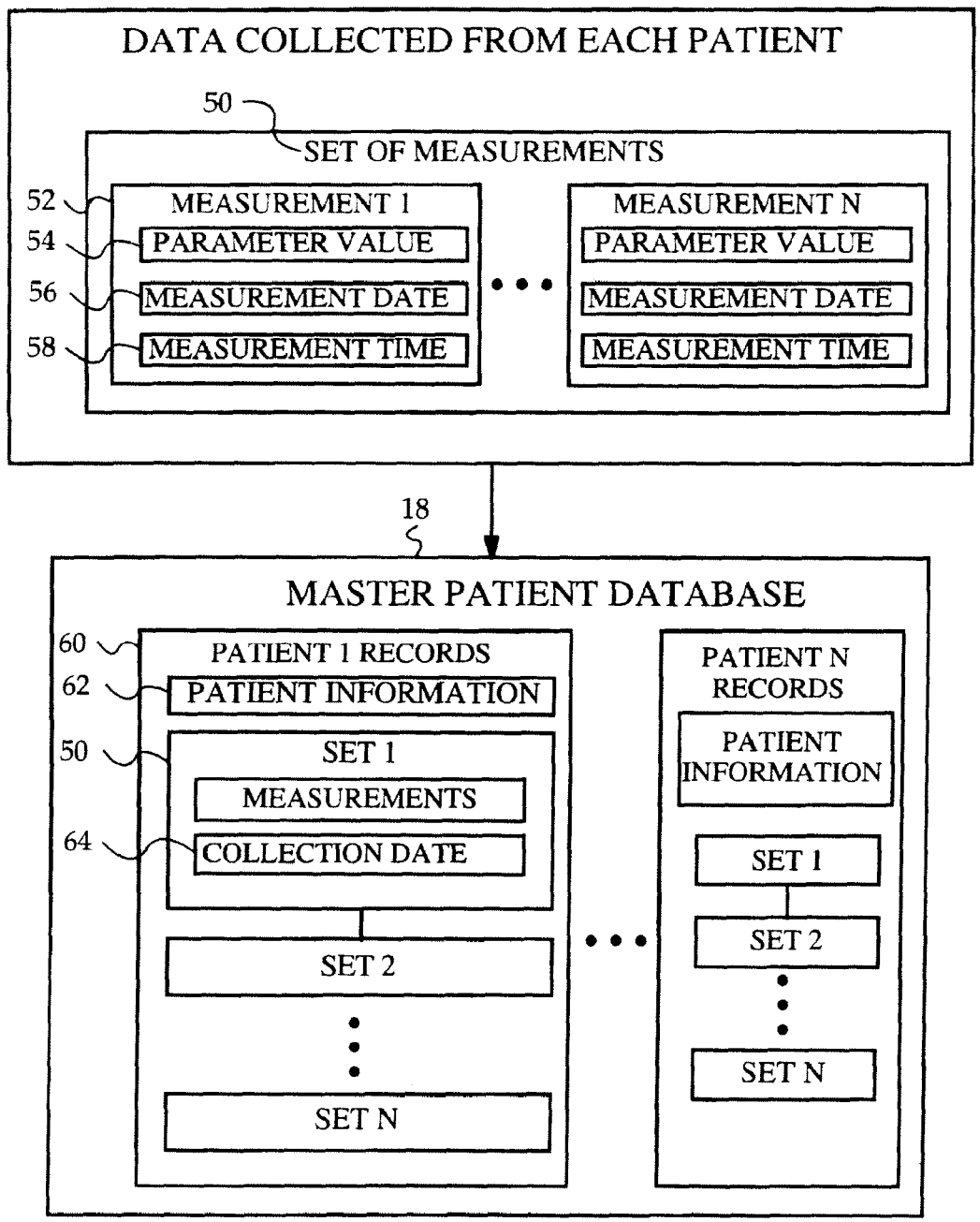
FIG. 2 is a schematic block diagram illustrating the collecting of data from each patient according to the invention.

FIG. 2 is a schematic block diagram illustrating the data which is collected from each patient and stored in master patient database 18. The data collected from each patient includes at least one corresponding set of measurements 50 of the control parameter of the health condition. Each set of measurements 50 includes at least one measurement 52. Each measurement 52 includes a measured control parameter value 54, such as a blood glucose level for a diabetic patient, a peak flow rate for an asthmatic patient, or a blood pressure reading for a hypertension patient. Each measurement 52 further includes a measurement date 56 and a measurement time 58.

The actual number of measurements in each set varies in dependence upon the nature of the health condition being monitored and the duration of time over which the measurements are recorded. For example, diabetic patients typically measure their blood glucose levels several times per day, so that these patients preferably record 20 to 40 measurements in a typical week of monitoring. However, hypertension patients may only be required to measure their blood pressure once a week, so that these patients would record only one measurement in a typical week of monitoring.

Each set of measurements 50 is transmitted to database 18. Database 18 stores patient records 60 for each patient participating in the monitoring system. Each patient's records include patient information 62 comprising a patient name, a patient telephone number, and a patient electronic mail address. Each patient's records also include each corresponding set of measurements 50 received from the patient. Each set 50 has a corresponding collection date 64.

In the preferred embodiment, collection date 64 is the date the corresponding set of measurements are received by clinic server 12. In an alternative embodiment, collection date 64 is the date the corresponding set of measurements are transmitted to the clinic. In another embodiment, collection date 64 is the measurement date 56 of a most recent measurement in the corresponding set of measurements.

Overview application 20 is designed to perform various calculations and comparisons using the patient data stored in database 18. First, overview application 20 is designed to calculate a control value for each patient from the patient's at least one corresponding set of measurements. Each control value indicates the corresponding patient's control over the health condition. In the preferred embodiment, the control value calculated for each patient is a mean value of the control parameter values recorded by the patient over a preselected period of time. In an alternative embodiment; the control value calculated for each patient is a mean value of the control parameter values in a set of measurements most recently collected from the patient.

The preselected period of time used to calculate the control value varies in dependence upon the nature of the patient's health condition. For example, a useful period of time for calculating a mean blood glucose value for diabetes patients is typically one week, while a useful period of time for calculating a mean daily number of panic attacks for phobic patients is typically two weeks. The actual period of time used to calculate the control value is preselected and programmed in overview application 20 according to guidelines prescribed by the clinician.

Second, overview application 20 is designed to determine for each patient a time period which has elapsed since the collection date of the set of measurements most recently collected from the patient. For example, if a patient has only transmitted to the clinic one set of measurements, overview application 20 determines the time that has elapsed since the collection date of the one set. If a patient has transmitted to the clinic multiple sets of measurements, overview application 20 determines the time that has elapsed since the most recent collection date.

Third, overview application 20 is designed to determine the compliance of each patient with a clinician prescribed measurement regimen. The prescribed measurement regimen preferably includes prescribed measurement dates and prescribed measurement times. To determine the compliance of each patient, overview application 20 compares each patient's actual measurement dates and times with the prescribed measurement dates and times.

For example, it is usually important that a diabetic patient measure his or her fasting blood glucose level every morning before breakfast. Thus one prescribed measurement time for a diabetes patient is 7 am, or similar pre-breakfast time. Overview application 20 compares the diabetes patient's actual measurement times with the prescribed pre-breakfast time to ensure that the patient is complying with the measurement regimen. Of course, many other prescribed measurement regimens are possible and are selected according to guidelines provided by the clinician.

In the preferred embodiment, the prescribed measurement regimen also includes a prescribed number of measurements to be taken by the patient over a prescribed time period. Overview application 20 is further capable of determining a completeness of each set of measurements relative to the prescribed measurement regimen.

Continuing with the example of the diabetic patient, a typical prescribed measurement regimen requires 3 measurements of the patient's blood glucose level per day. In this example, overview application 20 compares the actual number of measurements recorded by the patient on each measurement date to the three prescribed measurements per day to determine the completeness of the set. Specific techniques for writing and implementing an overview application that performs the calculations and comparisons described above are well known in the art.

Figure 3:
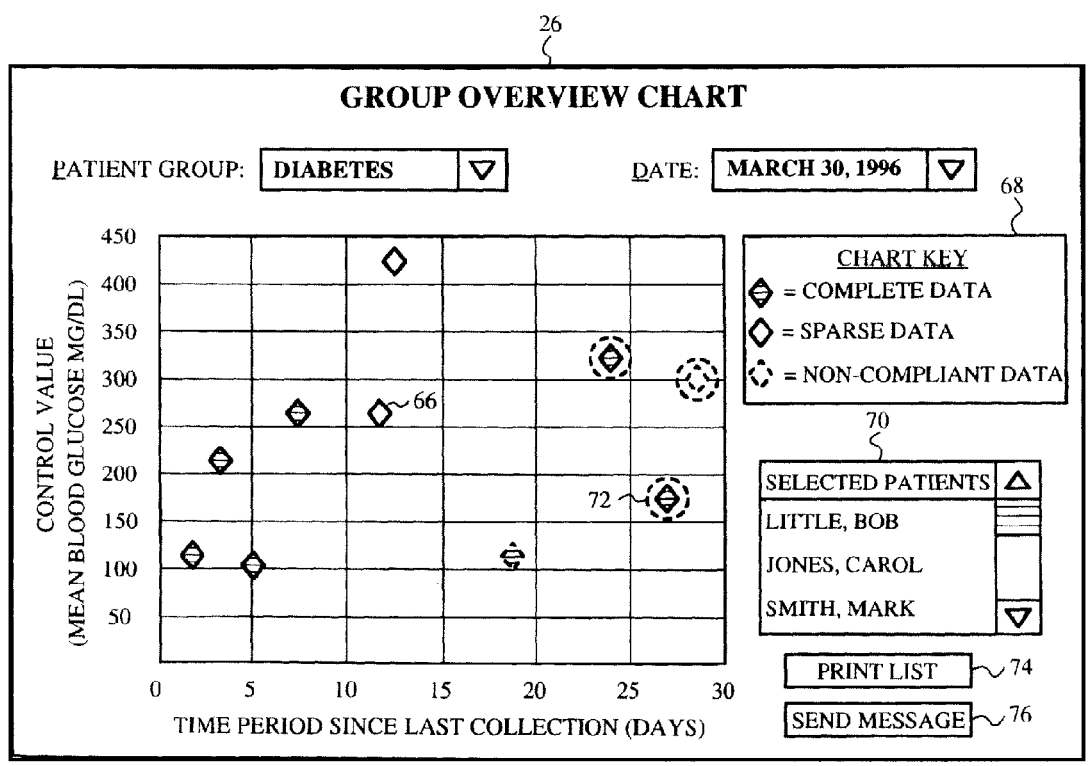
FIG. 3 is a sample group overview chart according to the invention.

Overview application 20 is further capable of generating group overview chart 26. FIG. 3. illustrates a sample group overview chart generated for a group of ten diabetes patients. Chart 26 has ten data points, each data point representing one corresponding patient and indicating the control value calculated for the patient and the time period elapsed since the patient's most recent collection date. In the preferred embodiment, each data point is represented on chart 26 by a corresponding icon 66.

Each icon 66 indicates the compliance of the corresponding patient with the prescribed measurement regimen. A chart key 68 is provided on chart 26 to explain the significance of each icon's appearance. Non-compliant patients are represented by flashing icons, while compliant patients are represented by non-flashing icons. In FIG. 3, the flashing icons having dotted borders, while the non-flashing icons have solid borders. In an alternative embodiment, non-compliant patients are represented by icons having a first color, while compliant patients are represented by icons having a second color.

Each icon 66 further indicates the completeness of the set of measurements most recently collected from the corresponding patient. Patients having complete sets are represented by filled icons, while patients having sparse sets are represented by blank icons. Of course, in alternative embodiments, the appearance of each icon 66 may be varied in alternative ways to indicate the compliance of the corresponding patient and the completeness of the corresponding patient's measurements.

Chart 26 further includes a list box 70, a print list button 74, and a send message button 76. List box 70 is for displaying a list of names of the patients selected from chart 26 by the clinician. The icons corresponding to the selected patients are highlighted, as represented by dotted circles 72. Print list button 74 is for sending the list of names to a printer (not shown) to obtain a print out of the list. Send message button 76 is for transmitting the list to mail merge application 14.

Referring to FIG. 4, mail merge application 14 is designed to generate for each selected patient a corresponding electronic mail message 78. Each message 78 contains supervisory instructions for the corresponding patient. Mail merge application 14 is capable of customizing each message 78 to include for the corresponding patient, the patient's name, the patient's electronic mail address, and the collection date of the patient's most recent set of measurements. The programming of a mail merge application to generate customized messages in this manner is well known in the art. FIG. 5 illustrates an alternative message 80 containing different instructions for each patient. Of course, messages containing many other instructions are possible in alternative embodiments.

Figure 6:
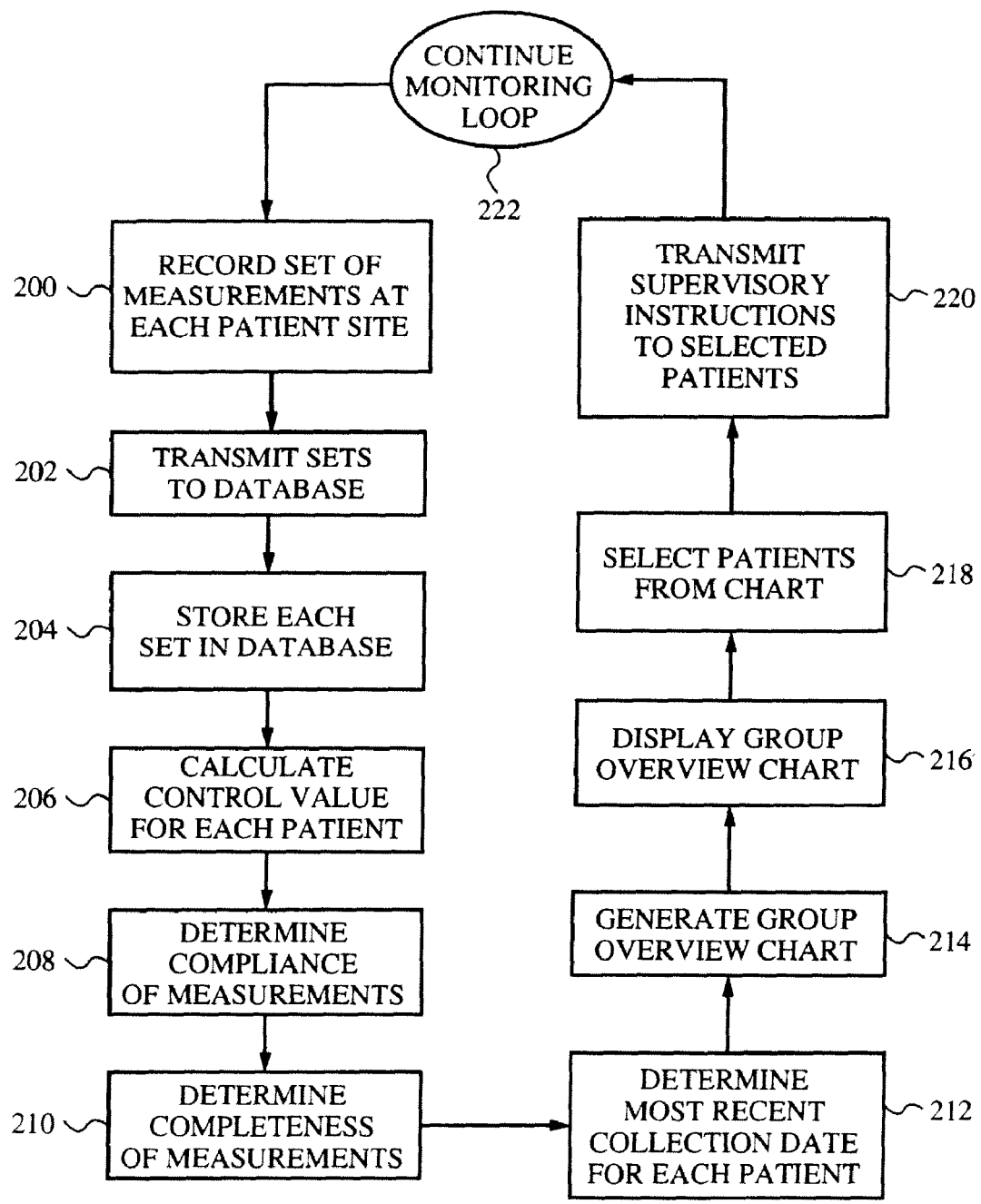
FIG. 6 is a flow chart illustrating steps included in the method of the invention.

The operation of the preferred embodiment is illustrated in FIG. 6. FIG. 6 is a flow chart showing a preferred method of using the system to monitor a group of patients having a health condition. Each patient is provided with a corresponding recording device, such as remote monitoring device 42 or electronic logbook 48. In step 200, each patient records in his or her recording device at least one corresponding set of measurements 50 of a control parameter of the health condition. In step 202, the recorded sets of measurements are transmitted from each recording device to database 18 through network 34. Each set of measurements is stored in database 18 with its corresponding collection date 64, step 204.

In step 206, overview application 20 calculates for each patient a control value from the patient's corresponding set of measurements. Next, application 20 determines the compliance of each patient with the prescribed measurement regimen by comparing the actual measurement times of the patient's corresponding measurements to the prescribed measurement times in the measurement regimen, step 208.

In step 210, application 20 determines for each patient the completeness relative to the prescribed measurement regimen of the corresponding set of measurements most recently collected from the patient. Application 20 then determines for each patient the time period which has elapsed since the corresponding collection date 64 of the set of measurements most recently collected from the patient, step 212.

Next application 20 generates group overview chart 26, step 214. In step 216, chart 26 is displayed on display 24, as shown in FIG. 3. Each data point on chart 26 is displayed as a corresponding icon 66. Each data point represents one corresponding patient and indicates the control value and the elapsed time period determined for the corresponding patient.

Each icon 66 indicates the compliance of the corresponding patient with the prescribed measurement regimen. Each icon 66 further indicates the completeness of the corresponding set of measurements most recently collected from the corresponding patient. Thus chart 26 allows clinician 30 to easily determine which patients in the group have been out of contact with clinic 10, which patients are having the greatest difficulty in controlling the health condition, and which patients are having difficulty complying with the prescribed treatment plan.

Next, clinician 30 uses selection device 28 to select from chart 26 at least one of the patients represented thereon, step 218. Typically, selection device 28 is a mouse or similar pointing device, and clinician 30 selects patients from chart 26 by clicking the icon corresponding to the patient. As clinician 30 selects each patient, list box 78 displays the name of each selected patient. Next clinician 30 selects send message button 76 to transmit the list of selected patients to mail merge application 14.

Application 14 generates for each selected patient corresponding electronic mail message 78. Each message 78 contains supervisory instructions for the corresponding patient. Mail merge application 14 customizes each message 78 to include for the corresponding patient, the patient's name, the patient's electronic mail address, and the collection date of the patient's most recent set of measurements. In step 220, mail server application 16 transmits each message 78 through network 34 to the corresponding patient. When the patients receive the supervisory instructions, they continue the monitoring loop with clinician 30, step 226, by returning to step 200 and repeating the method described.

The advantage of the multiple patient monitoring system of the preferred embodiment is that it allows the clinician to view and manage the medical priorities of an entire group of patients simultaneously. It also allows the clinician to communicate proactively with unmotivated patients who have lost contact with the clinician before these patients develop urgent medical needs. Consequently, the system allows the clinician to optimize efforts and minimize costs in managing the care of the entire group of patients.

Figures 7, 8:
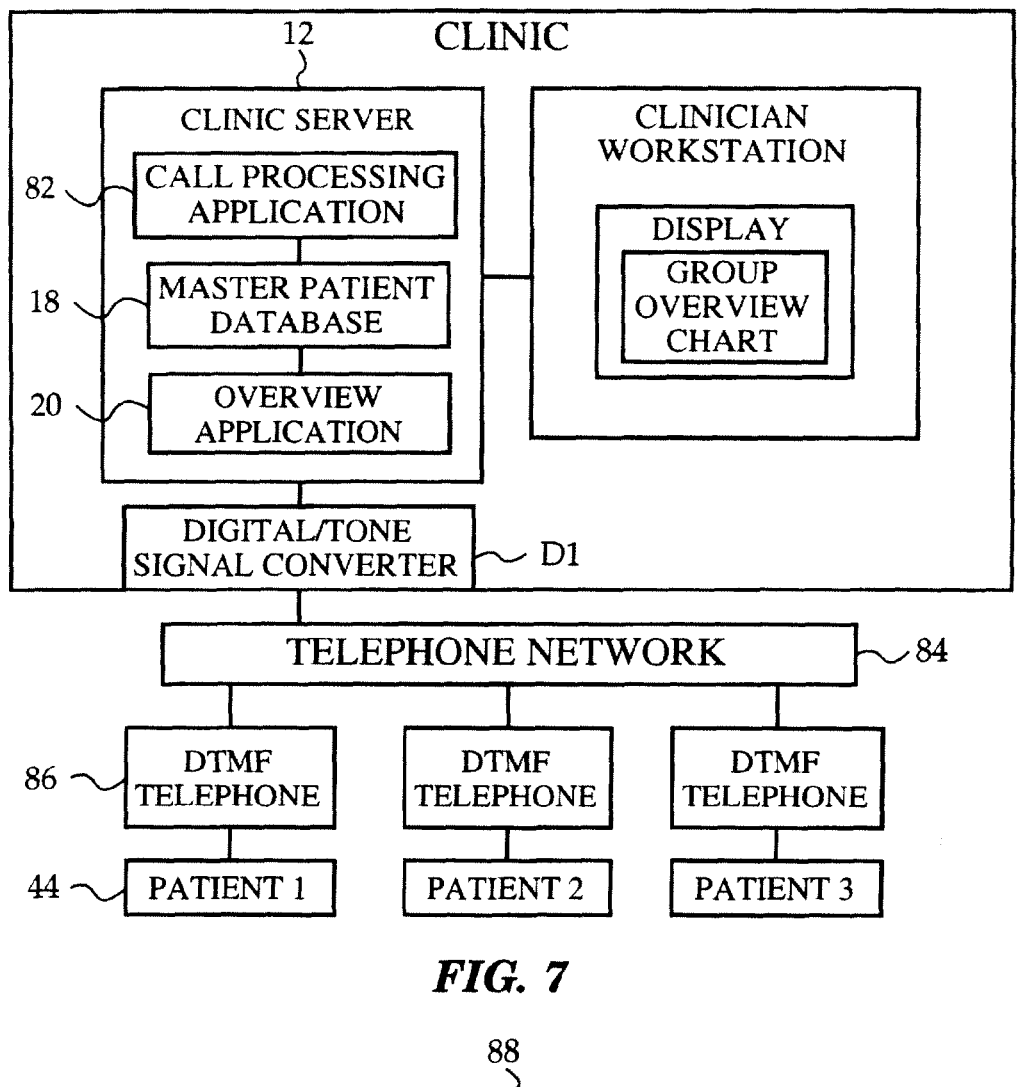
FIG. 7 is a schematic block diagram of another multiple patient monitoring system according to the invention.
FIG. 8 is a sample telephone message containing supervisory instructions for a patient.

A second embodiment of the invention is shown in FIGS. 7-8. The second embodiment differs from the preferred embodiment in the method of transmitting supervisory instructions to each patient selected from chart 26. Referring to FIG. 7, clinic server 12 includes an automated telephone call processing application 82 in place of mail merge application 14 and mail server application 16. Call processing application 82 is designed to generate for each selected patient a corresponding automated telephone message 88, as shown in FIG. 8. Each message 88 contains supervisory instructions for the corresponding patient.

Application 82 is capable of customizing each message 88 to include for the corresponding patient the patient's name and the collection date of the patient's most recent set of measurements. The programming of an automated call processing application to generate customized messages in this manner is well known in the art. Referring again to FIG. 7, clinic server 12 is connected to a telephone network 84 through a digital/tone signal converter D1. Each patient is provided with a dual tone multi-frequency telephone 86. Each telephone 86 is connected to telephone network 84 to receive automated telephone messages from clinic server 12.

The operation of the second embodiment differs from the operation of the preferred embodiment in that supervisory instructions are transmitted to the selected patients in automated telephone messages rather than in electronic mail messages. Otherwise, the operation and advantages of the second embodiment are identical to those of the preferred embodiment described above.

SUMMARY, RAMIFICATIONS, AND SCOPE

Although the above description contains many specificities, these should not be construed as limitations on the scope of the invention but merely as illustrations of the presently preferred embodiment. Many other embodiments of the invention are possible. For example, in one alternative embodiment, each software application located on the clinic server is loaded onto the clinician workstation, and the clinic server is eliminated from the system. The clinic server is presently preferred for performing resource intensive operations, such as storing large amounts of patient data, but the clinic server is not necessary to enable the system and method of the invention. In embodiments that include the clinic server, the clinic server need not be physically located at the clinic. The server may be located off-site and networked to the clinician computer.

Additionally, the preferred embodiment describes the use of remote monitoring devices and electronic logbooks for collecting data from each patient. However, many other methods of collecting data from patients are possible in alternative embodiments. For example, the patients could be provided with a paper based logbook and an automated reader for digitizing and transmitting the logbook information to the patient database. Alternatively, each patient could mail or fax the logbook information to the clinic for entry into the patient database. In another embodiment, the patients use DTMF telephones to connect to the patient database and enter their data through the telephone keypads.

Further, the electronic mail messages and automated telephone message illustrated are exemplary of just one possible embodiment of the invention. Many other messages may be generated and transmitted to patients in alternative embodiments. Additionally, the preferred embodiment describes a system and method for monitoring patients having diabetes. However, the invention is not limited to monitoring diabetic patients. The system and method described are equally effective for monitoring patients having asthma, hypertension, cardiovascular disease, eating disorders, HIV, mental health disorders, or any other health condition having a measurable control parameter.

Therefore, the scope of the invention should be determined not by the examples given but by the appended claims and their legal equivalents.

I claim:

1. A system for monitoring a plurality of patients regarding a health condition, comprising:

a reception unit for receiving a corresponding set of measurements regarding said health condition from each patient included in the plurality of patients;

a processing unit in communication with said reception unit for processing said corresponding set of measurements and identifying at least one patient included in the plurality of patients based upon said processing of said corresponding set of measurements;

a database, the database being in communication with said processing unit, the database being configured for storing medical health history information for each patient included in the plurality of patients, wherein processing of said corresponding set of measurements by the processing unit includes evaluating said corresponding set of measurements against said stored medical health history information;

a transfer unit in communication with said processing unit, wherein said transfer unit communicates with said at least one identified patient, said transfer unit being configured for transmitting a message for communicating with said at least one identified patient, the message being based upon said medical health history information and said processing of said corresponding set of measurements, the message being one of: a telephone message and an electronic mail message; and a display unit in communication with said processing unit, the display unit being configured for displaying a group overview chart, said group overview chart being generated by the processing unit based upon said processing and being provided to said display unit, said group overview chart including a plurality of data points, wherein each of the data points represents one corresponding patient included in the plurality of patients and indicates at least one control value for the one corresponding patient, the control value being indicative of the one corresponding patient's control over said health condition, the control value being based upon said corresponding set of measurements, each data point including an icon.

2. The system of claim 1, wherein said processing unit determines compliance based upon a time of receipt of said set of corresponding set of measurements and a number of corresponding sets of measurements compared with a prescribed number.

3. The system of claim 1, further comprising a device in communication with said reception unit.

4. The system of claim 3, wherein said device is one of a remote monitoring system or an electronic logbook.

5. The system of claim 4, further comprising a response device in communication with said transfer unit.

6. The system of claim 5, wherein said response device is at least one of a personal computer, a network terminal, a television, a personal digital assistant, or a video game system.

7. The system as claimed in claim 1, wherein said reception unit is a modem.

8. The system as claimed in claim 7, wherein said processing unit is a server.

9. The system as claimed in claim 8, wherein said display unit is a workstation.

* * * * *

Disclaimer

7,769,605 B2 - Stephen J. Brown, Woodside, CA (US). MULTIPLE PATIENT MONITORING SYSTEM FOR PROACTIVE HEALTH MANAGEMENT. Patent dated August 3, 2010. Disclaimer filed November 25, 2016, by the assignee, Robert Bosch LLC.

The term of this patent shall not extend beyond the expiration date of Patent No. 6,246,992.

*(Official Gazette, January 6, 2026)*

(12) EX PARTE REEXAMINATION CERTIFICATE (10637th)
United States Patent
Brown

(10) Number: US 7,769,605 C1
(45) Certificate Issued: *Jun. 22, 2015

(54) MULTIPLE PATIENT MONITORING SYSTEM FOR PROACTIVE HEALTH MANAGEMENT

(75) Inventor: Stephen J. Brown, Woodside, CA (US)

(73) Assignee: ROBERT BOSCH HEALTHCARE SYSTEMS, INC., Farmington, MI (US)

Reexamination Request:
No. 90/013,167, Apr. 2, 2014

Reexamination Certificate for:
Patent No.: 7,769,605
Issued: Aug. 3, 2010
Appl. No.: 11/843,727
Filed: Aug. 23, 2007

(*) Notice: This patent is subject to a terminal disclaimer.

Related U.S. Application Data

(63) Continuation of application No. 11/484,211, filed on Jul. 11, 2006, now Pat. No. 7,778,845, which is a continuation of application No. 10/233,296, filed on Aug. 30, 2002, now Pat. No. 7,970,620, which is a continuation-in-part of application No. 09/880,735, filed on Jun. 12, 2001, now abandoned, which is a continuation of application No. 09/152,353, filed on Sep. 14, 1998, now Pat. No. 6,246,992, which is a continuation-in-part of application No. 08/732,158, filed on Oct. 16, 1996, now Pat. No. 5,832,448.

(51) Int. Cl.
- *A61B 5/00* (2006.01)
- *G06F 19/00* (2011.01)
- *G06Q 10/10* (2012.01)
- *G06Q 50/24* (2012.01)
- *G06Q 50/22* (2012.01)

(52) U.S. Cl.
CPC .......... *A61B 5/0002* (2013.01); *G06F 19/3431* (2013.01); *G06Q 10/10* (2013.01); *G06F 19/322* (2013.01); *G06Q 50/24* (2013.01); *G06Q 50/22* (2013.01); *G06F 19/3418* (2013.01); *G06F 19/3456* (2013.01); *G06F 19/3487* (2013.01); *G06F 19/327* (2013.01)

(58) Field of Classification Search
None
See application file for complete search history.

(56) References Cited

To view the complete listing of prior art documents cited during the proceeding for Reexamination Control Number 90/013,167, please refer to the USPTO's public Patent Application Information Retrieval (PAIR) system under the Display References tab.

*Primary Examiner* — Behzad Peikari

(57) ABSTRACT

A system and method for monitoring a group of patients having a chronic disease or ongoing health condition. The method includes the step of collecting from each patient a corresponding set of measurements of a control parameter of the health condition. Each set of measurements has a collection date. A control value is calculated for each patient from the corresponding set of measurements. The method further includes the steps of generating and displaying a group overview chart having one data point for each patient. Each data point indicates the control value calculated for the corresponding patient and a time period which has elapsed since the collection date of the patient's corresponding set of measurements. In a preferred embodiment, the method includes the additional steps of selecting from the group overview chart at least one of the patients represented thereon and transmitting supervisory instructions to the at least one selected patient.

At the time of issuance and publication of this certificate, the patent remains subject to pending reexamination control number 90/013,484 filed Apr. 2, 2015. The claim content of the patent may be subsequently revised if a reexamination certificate issues from the reexamination proceeding.

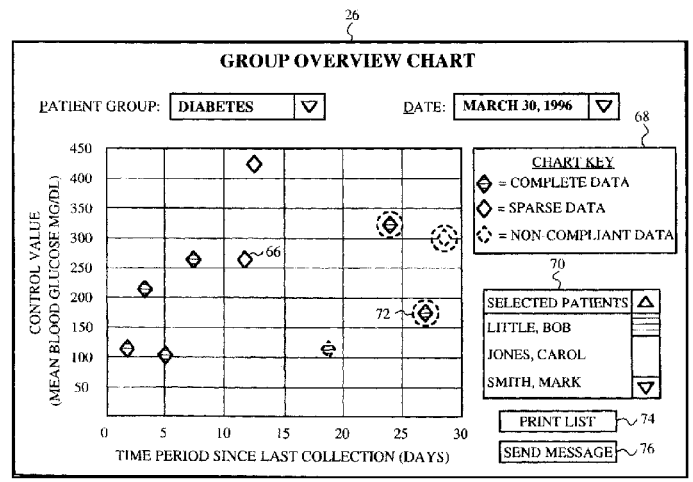

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-9 is confirmed.

\* \* \* \* \*

(12) EX PARTE REEXAMINATION CERTIFICATE (10838th)
United States Patent
Brown

(10) Number: US 7,769,605 C2
(45) Certificate Issued: *Mar. 30, 2016

(54) MULTIPLE PATIENT MONITORING SYSTEM FOR PROACTIVE HEALTH MANAGEMENT

(75) Inventor: Stephen J. Brown, Woodside, CA (US)

(73) Assignee: ROBERT BOSCH HEALTHCARE SYSTEMS, INC., Farmington, MI (US)

Reexamination Request:
No. 90/013,484, Apr. 2, 2015

Reexamination Certificate for:
Patent No.: 7,769,605
Issued: Aug. 3, 2010
Appl. No.: 11/843,727
Filed: Aug. 23, 2007

Reexamination Certificate C1 7,769,605 issued Jun. 22, 2015

(*) Notice: This patent is subject to a terminal disclaimer.

Related U.S. Application Data

(63) Continuation of application No. 11/484,211, filed on Jul. 11, 2006, now Pat. No. 7,778,845, which is a continuation of application No. 10/233,296, filed on Aug. 30, 2002, now Pat. No. 7,970,620, which is a continuation-in-part of application No. 09/880,735, filed on Jun. 12, 2001, now abandoned, which is a continuation of application No. 09/152,353, filed on Sep. 14, 1998, now Pat. No. 6,246,992, which is a continuation-in-part of application No. 08/732,158, filed on Oct. 16, 1996, now Pat. No. 5,832,448.

(51) Int. Cl.
*A61B 5/00* (2006.01)
*G06F 19/00* (2011.01)
*G06Q 50/24* (2012.01)
*G06Q 10/10* (2012.01)
*G06Q 50/22* (2012.01)

(52) U.S. Cl.
CPC .......... *G06F 19/3487* (2013.01); *A61B 5/0002* (2013.01); *G06F 19/322* (2013.01); *G06F 19/3418* (2013.01); *G06F 19/3431* (2013.01); *G06Q 10/10* (2013.01); *G06Q 50/22* (2013.01); *G06Q 50/24* (2013.01); *G06F 19/327* (2013.01); *G06F 19/3456* (2013.01)

(58) Field of Classification Search
None
See application file for complete search history.

(56) References Cited

To view the complete listing of prior art documents cited during the proceeding for Reexamination Control Number 90/013,484, please refer to the USPTO's public Patent Application Information Retrieval (PAIR) system under the Display References tab.

*Primary Examiner* — Behzad Peikari

(57) ABSTRACT

A system and method for monitoring a group of patients having a chronic disease or ongoing health condition. The method includes the step of collecting from each patient a corresponding set of measurements of a control parameter of the health condition. Each set of measurements has a collection date. A control value is calculated for each patient from the corresponding set of measurements. The method further includes the steps of generating and displaying a group overview chart having one data point for each patient. Each data point indicates the control value calculated for the corresponding patient and a time period which has elapsed since the collection date of the patient's corresponding set of measurements. In a preferred embodiment, the method includes the additional steps of selecting from the group overview chart at least one of the patients represented thereon and transmitting supervisory instructions to the at least one selected patient.

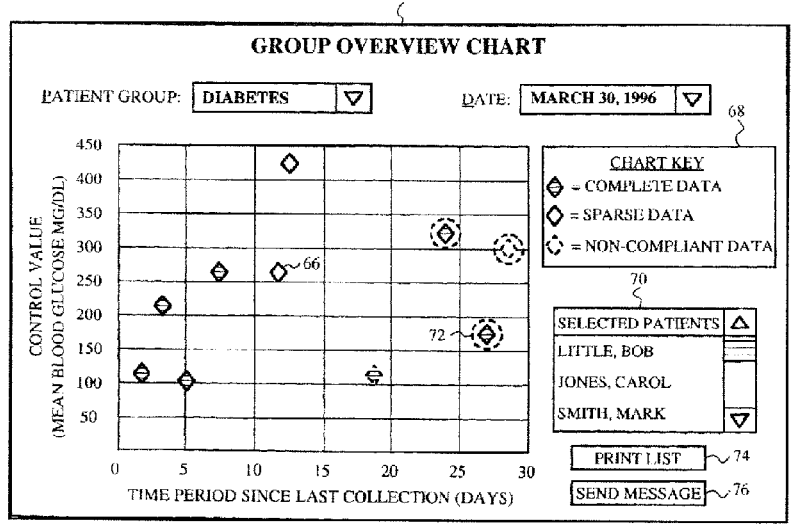

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1-9 is confirmed.

\* \* \* \* \*

(12) EX PARTE REEXAMINATION CERTIFICATE (11200th)
United States Patent
Brown

(10) Number: US 7,769,605 C3
(45) Certificate Issued: *Oct. 23, 2017

(54) MULTIPLE PATIENT MONITORING SYSTEM FOR PROACTIVE HEALTH MANAGEMENT

(75) Inventor: Stephen J. Brown, Woodside, CA (US)

(73) Assignee: ROBERT BOSCH LLC, Palo Alto, CA (US)

Reexamination Request:
No. 90/013,769, Jun. 17, 2016
No. 90/013,773, Jun. 29, 2016

Reexamination Certificate for:
Patent No.: 7,769,605
Issued: Aug. 3, 2010
Appl. No.: 11/843,727
Filed: Aug. 23, 2007

Reexamination Certificate C1 7,769,605 issued Jun. 22, 2015

Reexamination Certificate C2 7,769,605 issued Mar. 30, 2016

(*) Notice: This patent is subject to a terminal disclaimer.

Related U.S. Application Data

(63) Continuation of application No. 11/484,211, filed on Jul. 11, 2006, now Pat. No. 7,778,845, which is a continuation of application No. 10/233,296, filed on Aug. 30, 2002, now Pat. No. 7,970,620, which is a continuation-in-part of application No. 09/880,735, filed on Jun. 12, 2001, now abandoned, which is a continuation of application No. 09/152,353, filed on Sep. 14, 1998, now Pat. No. 6,246,992, which is a continuation-in-part of application No. 08/732,158, filed on Oct. 16, 1996, now Pat. No. 5,832,448.

(51) Int. Cl.
*A61B 5/00* (2006.01)
*G06F 19/00* (2011.01)
*G06Q 50/22* (2012.01)
*G06Q 50/24* (2012.01)
*G06Q 10/10* (2012.01)

(52) U.S. Cl.
CPC ........ *G06F 19/3487* (2013.01); *A61B 5/0002* (2013.01); *G06F 19/322* (2013.01); *G06F 19/3418* (2013.01); *G06F 19/3431* (2013.01); *G06Q 10/10* (2013.01); *G06Q 50/22* (2013.01); *G06Q 50/24* (2013.01); *G06F 19/327* (2013.01); *G06F 19/3456* (2013.01)

(58) Field of Classification Search
None
See application file for complete search history.

(56) References Cited

To view the complete listing of prior art documents cited during the proceedings for Reexamination Control Numbers 90/013,769 and 90/013,773, please refer to the USPTO's public Patent Application Information Retrieval (PAIR) system under the Display References tab.

*Primary Examiner* — Jeffrey Carlson

(57) ABSTRACT

A system and method for monitoring a group of patients having a chronic disease or ongoing health condition. The method includes the step of collecting from each patient a corresponding set of measurements of a control parameter of the health condition. Each set of measurements has a collection date. A control value is calculated for each patient from the corresponding set of measurements. The method further includes the steps of generating and displaying a group overview chart having one data point for each patient. Each data point indicates the control value calculated for the corresponding patient and a time period which has elapsed since the collection date of the patient's corresponding set of measurements. In a preferred embodiment, the method includes the additional steps of selecting from the group overview chart at least one of the patients represented thereon and transmitting supervisory instructions to the at least one selected patient.

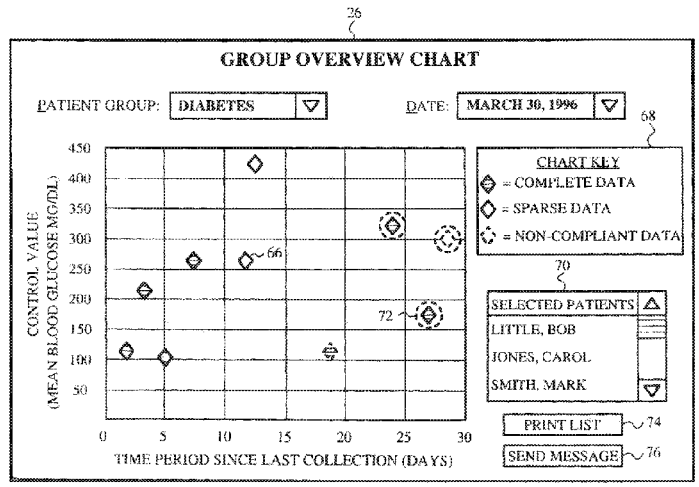

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-9 are cancelled.

* * * * *